United States Patent
Leppert et al.

(10) Patent No.: US 6,933,119 B2
(45) Date of Patent: Aug. 23, 2005

(54) METHODS AND COMPOSITIONS FOR THE DETECTION AND TREATMENT OF MULTIPLE SCLEROSIS

(75) Inventors: David Leppert, Binningen (CH); Raija Lindberg, Zuzgen (CH)

(73) Assignee: Roche Molecular Systems, Inc., Alameda, CA (US)

( * ) Notice: Subject to any disclaimer, the term of this patent is extended or adjusted under 35 U.S.C. 154(b) by 27 days.

(21) Appl. No.: 10/238,474

(22) Filed: Sep. 10, 2002

(65) Prior Publication Data

US 2003/0054397 A1 Mar. 20, 2003

(30) Foreign Application Priority Data

Sep. 12, 2001 (EP) ............................................ 01121921

(51) Int. Cl.⁷ ........................... C12Q 1/68; C12P 19/34; C07H 21/02
(52) U.S. Cl. ......................... 435/6; 435/91.1; 435/91.2; 536/23.1; 536/24.3; 536/24.31; 536/24.33
(58) Field of Search .......................... 435/6, 91.1, 91.2, 435/7.2; 536/23.1, 24.3, 24.31, 24.33; 530/350

(56) References Cited

U.S. PATENT DOCUMENTS

| 5,721,351 A | 2/1998 | Levinston |
| 6,335,170 B1 * | 1/2002 | Orntoft ........................... 435/6 |

FOREIGN PATENT DOCUMENTS

| WO | WO 98/24935 | 6/1998 |
| WO | WO 00/70099 | 11/2000 |
| WO | WO 02/079218 | 10/2002 |

OTHER PUBLICATIONS

Waubant et al. Relationship between serum levels of IL–10, MRI activity and interferon beta–1a therapy in patients with relapsing remitting MS. Journal of Neuroimmunology, vol. 112, pp. 139–145, published online Dec. 4, 2000, Journal Jan. 2001).*
International Preliminary Examination Report dated Mar. 8, 2004, issued by the International Preliminary Examining Authority in the corresponding PCT application.
Whitney Laurie Ward, et al., Annals of Neurology, vol. 46, No. 3, pp. 425–428, XP009009149 (1999).
Ibrahim S.M., et al, Brain 2001 United Kingdom, vol. 124, No. 10, pp. 1927–1938, XP008020655 (2001).
Grekova Maria C., et al., Annals of Neurology, vol. 40, No. 1, pp. 108–112, XP008020622 (1996).
Steinman L., Advances in Experimental Medicine and Biology, United States 2001, vol. 490, pp. 109–112, XP008020619 (2001).
Bomprezzi R., et al., International MS Journal 1999 United Kingdom, vol. 6, No. 2, pp. 42–49, XP008020652 (1999).
Ward Yvona, et al., Nature (London), vol. 367, No. 6464, pp. 651–654, XP002250847 (1994).
Lindberg et al., Mulitple Sclerosis 7 (Suppl. 7), S73 (P223), 2001.

* cited by examiner

Primary Examiner—Cynthia Wilder
(74) Attorney, Agent, or Firm—Bart W. Wise; Rhea C. Nersesian; Robert W. Mann

(57) ABSTRACT

The present invention relates to an in vitro method for the diagnosis of multiple sclerosis and/or the susceptibility to multiple sclerosis comprising the steps of a) obtaining a biological sample; and b) detecting and/or measuring the increase, decrease and/or absence of (a) specific marker gene(s) as disclosed herein.

11 Claims, No Drawings

METHODS AND COMPOSITIONS FOR THE DETECTION AND TREATMENT OF MULTIPLE SCLEROSIS

BACKGROUND OF THE INVENTION

The present invention relates to an in vitro method for the diagnosis of multiple sclerosis and/or the susceptibility to multiple sclerosis comprising the steps of a) obtaining a biological sample; and b) detecting and/or measuring the increase, decrease and or absence of (a) specific marker gene(s) as disclosed herein. Furthermore, screening methods relating to inhibitors, activators, antagonists as well as agonists of the specific marker genes disclosed herein are provided. In addition pharmaceutical and diagnostic compositions are disclosed.

Multiple sclerosis (MS) is a chronic autoimmune disease of the CNS. It is characterized by focal inflammation, demyelination and a variable degree of axonal loss and neuronal damage. Genomic analysis indicates that susceptibility for MS is related to several not yet identified genes. Incomplete penetrance of presumed MS susceptibility genes and genetic heterogeneity have prevented to define any specific markers for the diagnosis and the course of MS.

Brain tissue destruction occurs very early in the course of disease, when the damage is still clinically silent. Therefore, early diagnostic markers are needed as well as predictive markers for relapses to design the treatment according to disease activity. Because of the immunological characteristics of the disease several attempts to define immunological parameters for MS have been made. Blood brain barrier (BBB) breakdown and invasion of T cells into CNS are the early events of MS pathogenesis. There is an increasing body of evidence that interaction of various molecules are involved in the transendothelial migration of immune cells. These molecules comprise adhesion molecules, matrix metalloproteinases (MMPs), cytokines and chemokines. Magnetic resonance imaging (MRI) has provided the possibility to examine inflammatory activity and axonal alterations in CNS in vivo.

Several studies have shown that increase of MMP-9 in serum and cerebrospinal fluid (CSF) is correlated with disease course and with new gadolinium-enhancing lesions measured with MRI. The activity of MMPs is strictly controlled by endogenous tissue inhibitors of metalloproteinases (TIMPs). In fact, it has been demonstrated that increased MMP-9 and decreased TIMP1 levels are risk factors for formation of new gadolinium-enhancing lesions.

Whereas the above discussed two proteins are known to increase the risk of gadolinium-enhanced lesions when increased or decreased, respectively, there is still a need for specific means and methods for safe and reliable diagnosis of multiple sclerosis as well as for the development of effective means of therapeutic intervention in said chronic disorder. Therefore, the technical problem underlying the present invention was to provide for diagnostic markers as well as for therapeutic targets for multiple sclerosis.

SUMMARY OF THE INVENTION

Accordingly, the present invention provides an in vitro method for the diagnosis of multiple sclerosis and/or detecting the susceptibility to multiple sclerosis comprising the steps of a) obtaining a biological sample; b) detecting and/or measuring the increase, decrease and or absence of (a) specific marker gene(s) as listed in Table 2 below.

In the present invention, it was surprisingly found that a specific set of marker genes are differentially expressed in cells/tissues obtained from individuals suffering from multiple sclerosis (MS). Said differentially expressed marker genes are listed in Table 2 below. These marker genes comprise No. 1 to 22 and 26 to 31 as depicted in Table 2.

DETAILED DESCRIPTION OF THE INVENTION

The term "differentially expressed" in accordance with this invention relates to marker genes which are either up- or downregulated in tissues and or cells derived form MS individuals/patients or individuals susceptible for MS in comparison to healthy individuals or individuals which do not suffer from MS or are not prone to suffer from MS.

As illustrated in appended Table 2 and in the appended examples, specific marker genes which are upregulated comprise, but are not limited to: Nos. 1 to 15, 17 to 20 and 26 to 31 as depicted in Table 2.

Marker genes which are downregulated in MS comprise, but are not limited to Nos. 16, 21 and 22 as depicted in Table 2.

In accordance with the present invention, the term "biological sample" as employed herein means a sample which comprises material wherein said differential expression of marker genes may be measured and may be obtained from an individual. Particular preferred samples comprise body fluids, like blood, sera, plasma, urine, synovial fluid, spinal fluid, cerebrospinal fluid, semen or lymph, as well as body tissues, preferably brain and nervous tissue. Particularly preferred and as documented in the appended examples are peripheral blood samples, more particular peripheral blood mononuclear cells (PBMCs).

The detection and/or measurement of the differentially expressed marker genes may comprise the detection of an increase, decrease and/or the absence of a specific nucleic acid molecule, for example RNA or cDNA, the measurement/detection of a expressed polypeptide/protein as well as the measurement/detection of a (biological) activity (or lack thereof) of the expressed protein/polypeptide. Said (biological) activity may comprise enzymatic activities, activities relating to signaling pathway-events e.g. antigen-recognition as well as effector-events.

Methods for the detection/measurement of RNA and or cDNA levels are well known in the art and comprise methods as described in the appended examples. Such methods include, but are not limited to PCR-technology.

The differentially expressed marker genes may also be detected on the protein level by standard methods which comprise, but are not limited to, Western-blotting, ELISAs, RIAs, IRMAs, FIAs, CLIAs or ECLs.

In one embodiment, the method of the invention contemplates the detection/measurement of at least one marker gene listed in Table 2. In other embodiments, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven and/or at least twenty-eight marker genes as listed in Table 2 are detected/measured. It is furthermore envisaged that specific pattern of differentially expressed marker genes as depicted in Table 2 are detected, measured and/or compared. It is also envisaged that specific patterns of differentially expressed marker genes as depicted in Table 2 and 3 are detected, measured and/or compared. In this respect, at least one marker gene as listed in Table 2 is detected/measured in combination with at least one marker gene as depicted in Table 3.

It is also envisaged that the inventive method comprises the comparison of differentially expressed marker genes, i.e. marker genes which are up or downregulated in tissues, cells, body fluids etc, from MS-patients or individuals suspected to be MS patients, with markers which are not changed, i.e. which are not diagnostic for MS. Such unchanged marker genes comprise, inter alia the ribosomal RNA control as employed in the appended examples, as well as Nos. 32, 34, 35 and/or 36 as depicted in Table 4.

It is preferred that the detection and/or measuring step of the inventive method is carried out by detecting and/or measuring nucleic acid molecules coding for proteins/polypeptides encoded by the marker gene(s) as listed in the appended Tables 2, 3 and 4. Corresponding measuring/detection methods are well known in the art and also exemplified in the appended examples. Therefore, said method may comprise the measurement/detection of RNA-, mRNA or DNA-molecules. Preferably, said DNA is cDNA.

Yet, in another embodiment of the present invention, the inventive in vitro method comprises a method, wherein said detection and/or measuring step is carried out by detecting and/or measuring (a) protein(s)/(a) polypeptide(s) or a fragment thereof encoded by the gene(s) as listed in Tables 2, 3 and 4. Again, these detection/measuring steps comprise methods known in the art, like inter alia, proteomics, immuno-chemical methods like Western-blots, ELISAs and the like.

Preferably, in the in vitro method of the present invention the expression levels of at least two marker genes as listed in Table 2 are compared. It is also preferred in the in vitro method of the present invention that the expression levels of at least one marker gene as listed in Table 2 is compared with at least one marker gene as listed in Table 3. For example, it is envisaged that the inventive method comprises the measurement/detection of at least one up-regulated and at least one down-regulated marker gene or gene product.

Most preferably, the expression level of (a) marker gene (s) as listed in Table 2 in a biological sample from an individual suspected to suffer from multiple sclerosis and/or to be susceptible to multiple sclerosis is compared to the expression levels of the same marker gene(s) in a healthy individual. In another most preferred embodiment, the expression level of at least one marker gene as listed in Table 2 in combination with at least one marker gene as listed in Table 3 in the biological sample from an individual suspected to suffer from MS and/or to be susceptible to MS is compared to the expression levels of the same marker genes in a healthy individual.

In context of the present invention, the term "expression level" comprises, inter alia, the RNA-levels, i.e. the amount or quality of RNA, mRNA, the cDNA-levels, as well as the level and the quality of the corresponding expressed protein or polypeptide.

Most preferably, an increase or decrease of the expression level in (a) marker gene(s) as listed in Table 2 and as detected by the inventive method is indicative of multiple sclerosis or the susceptibility to multiple sclerosis. In another most preferred embodiment an increase or decrease of the expression level in at least one marker gene as listed in Table 2 together with an increase or decrease of at least one marker gene as listed in Table 3 and as detected by the inventive method is indicative of multiple sclerosis or the susceptibility to multiple sclerosis.

In another embodiment, the present invention provides for a screening method for identifying and/or obtaining a compound which is suspected to be an inhibitor or an antagonist of an expressed marker-gene as listed in Table 2 or 3 and whose expression is upregulated in multiple sclerosis, comprising the steps of (a) contacting said expressed marker gene or its expression product with a compound or a plurality of compounds suspected to be an inhibitor or antagonist of said expressed marker gene under conditions which allow interaction of said compound with said expressed marker gene; and (b) detecting the interaction between said compound or plurality of compounds with said expressed marker gene.

Furthermore, the invention provides for a screening method for identifying and/or obtaining a compound which is suspected to be an inhibitor or an antagonist of an expressed marker gene as listed in Table 2 or 3 and whose expression is upregulated in multiple sclerosis, comprising the steps of (a) contacting a host which expresses said marker gene with a compound suspected to be an inhibitor or antagonist of said expressed marker gene under conditions which allow interaction of said compound with said expressed marker gene;

(b) determining the activity of said marker gene;

(c) determining the activity of said marker gene in a host as defined in (a), which has not been contacted with said compound; and (d) quantitatively relating the activity as determined in (b) and (c), whereby a decreased activity determined in (b) in comparison to (c) is indicative for an inhibitor or antagonist.

In another embodiment, the invention also provides a screening method for identifying and/or obtaining a compound which is suspected to be an activator or an agonist of an expressed marker gene as listed in Table 2 and whose expression is downregulated in multiple sclerosis, comprising the steps of (a) contacting said expressed marker gene or its expression product with a compound or a plurality of compounds suspected to be an activator or agonist of said expressed marker gene or said expression product under conditions which allow interaction of said compound with said expressed marker gene or said expression product; and (b) detecting the interaction between said compound or plurality of compounds with said expressed marker gene or said expression product.

Furthermore, in another embodiment, the invention relates to a screening method for identifying and/or obtaining a compound which is suspected to be an activator or an agonist of an expressed marker gene as listed in Table 2 and whose expression is downregulated in multiple sclerosis, comprising the steps of (a) contacting a host which expresses said marker gene with a compound suspected to be an activator or agonist of said expressed marker gene under conditions which allow interaction of said compound with said expressed marker gene;

(b) determining the activity of said marker gene;

(c) determining the activity of said marker gene in a host as defined in (a), which has not been contacted with said compound; and (d) quantitatively relating the activity as determined in (b) and (c), whereby an increased activity determined in (b) in comparison to (c) is indicative for an activator or agonist.

The "interaction" in the screening methods as disclosed herein may be measured by conventional methods. Accordingly, interaction assays to be employed in the method disclosed herein may comprise FRET-assays (fluorescence resonance energy transfer; as described, inter alia, in Ng, Science 283 (1999), 2085–2089 or Ubarretxena-Belandia, Biochem. 38 (1999), 7398–7405), TR-FRETs and biochemical assays as disclosed herein. Furthermore, commercial assays like "Amplified Luminescent Proximity Homogenous Assay™" (BioSignal Packard) may be employed. Further methods are well known in the art and, inter alia, described in Fernandez, Curr. Opin. Chem. Biol. 2 (1998), 547–603.

The "test for interaction" may also be carried out by specific immunological and/or biochemical assays which are well known in the art and which comprise, e.g., homogenous and heterogenous assays as described herein below.

Said interaction assays employing read-out systems are well known in the art and comprise, inter alia, two-hybrid screenings (as, described, inter alia, in EP-0 963 376, WO 98/25947, WO 00/02911; and as exemplified in the appended examples), GST-pull-down columns, co-precipitation assays from cell extracts as described, inter alia, in Kasus-Jacobi, Oncogene 19 (2000), 2052–2059, "interaction-trap" systems (as described, inter alia, in U.S. Pat. No. 6,004,746) expression cloning (e.g. lamda gtII), phage display (as described, inter alia, in U.S. Pat. No. 5,541,109), in vitro binding assays and the like. Further interaction assay methods and corresponding read out systems are, inter alia, described in U.S. Pat. No. 5,525,490, WO 99/51741, WO 00/17221, WO 00/14271 or WO 00/05410. Vidal and Legrain (1999) in Nucleic Acids Research 27, 919–929 describe, review and summarize further interaction assays known in the art which may be employed in accordance with the present invention. These assays comprise in-hybrid systems.

Homogeneous (interaction) assays comprise assays wherein the binding partners remain in solution and comprise assays, like agglutination assays. Heterogeneous assays comprise assays like, inter alia, immuno assays, for example, ELISAs, RIAs, IRMAs, FIAs, CLIAs or ECLs.

The above mentioned host to be employed in the screening methods of the present invention and comprising and/or expressing a maker gene as defined herein may comprise a prokaryotic as well as an eukaryotic cell. Said cells may comprise bacterial cells, yeast cells, as well as cultured cell (tissue) lines, inter alia, derived from mammals. Furthermore animals may also be employed as hosts, for example an non-human transgenic animal.

Accordingly, said host (cell) may be transfected or transformed with the vector comprising a nucleic acid molecule coding for a marker gene of MS as disclosed herein. Said host cell or host may therefore be genetically modified with a nucleic acid molecule encoding such a marker gene or with a vector comprising such a nucleic acid molecule. The term "genetically modified" means that the host cell or host comprises in addition to its natural genome a nucleic acid molecule or vector as defined herein and coding for a marker gene for MS or at least a fragment thereof. Said additional genetic material may be introduced into the host (cell) or into one of its predecessors/parents. The nucleic acid molecule or vector may be present in the genetically modified host cell or host either as an independent molecule outside the genome, preferably as a molecule which is capable of replication, or it may be stably integrated into the genome of the host cell or host.

As mentioned herein above, the host cell of the present invention may be any prokaryotic or eukaryotic cell. Suitable prokaryotic cells are those generally used for cloning like $E.\ coli$ or $Bacillus\ subtilis$. Yet, these prokaryotic host cells are also envisaged in the screening methods disclosed herein. Furthermore, eukaryotic cells comprise, for example, fungal or animal cells. Examples for suitable fungal cells are yeast cells, preferably those of the genus Saccharomyces and most preferably those of the species $Saccharomyces\ cerevisiae$. Suitable animal cells are, for instance, insect cells, vertebrate cells, preferably mammalian cells, such as e.g. CHO, HeLa, NIH3T3 or MOLT-4. Further suitable cell lines known in the art are obtainable from cell line depositories, like the American Type Culture Collection (ATCC).

The hosts may also be selected from non-human mammals, most preferably mice, rats, sheep, calves, dogs, monkeys or apes. As described herein above, said animals/mammals also comprise non-human transgenic animals, which preferably express at least one marker gene for MS as disclosed herein. Preferably, said marker gene is a upregulated marker gene, i.e. a marker gene whose gene product is up-regulated in tissue derived from MS patients.

The present invention also contemplates that non-human transgenic animals be produced which do not express marker genes as disclosed herein or who express limited amounts of said marker gene products. Said animals are preferably related to marker genes which are down-regulated in cells, body fluids or tissues derived from MS-patients.

Transgenic non-human animals comprising and/or expressing the up-regulated marker gene of the present invention or, in contrast who comprise silenced or less efficient versions of down-regulated marker genes for MS, are useful models for studying MS-development and provide for useful models for testing drugs and therapeutics for MS-treatment and/or prevention.

The term "quantitatively relating" as employed herein above means that the activity of differentially expressed marker gene(s) which is determined in steps (b) and (c) of the above described inventive methods are compared. It is, inter alia, envisaged that the activity(ies) obtained when the compound to be identified and/or obtained by the inventive method is compared to the activity(ies) of a control which comprises the same experimental setting but wherein said compound is omitted. Said "quantitative relation" may be carried out by methods known to the skilled artisan, e.g. morphometric analysis, comparisons of protein patterns, phosphorylation status, etc. Furthermore, it is envisaged that said comparisons and/or quantitative relation is carried out in a computer-assisted fashion. Said comparison/quantitative relation may also comprise the analysis in high-throughput screens.

Inhibitors, antagonists, activators or agonists as identified and/or obtained by the methods of the present invention are particularly useful in the therapeutic management, prevention and or treatment of multiple sclerosis.

Said inhibitor and/or antagonist which is suspected to be an inhibitor or antagonist the marker genes and or gene products which are upregulated in MS and/or whose activity is upregulated in MS is preferably a compound that interacts and/or interferes with said marker genes or gene products. Said interaction may be a direct interaction, like a direct protein/protein or protein/nucleic acid molecule interaction, but it is also envisaged that said interaction-may be mediated by further, additional compounds.

Therefore, potential inhibitors or antagonists to be identified, screened for and/or obtained with the method of the present invention include molecules, preferably small molecules which bind to, interfere with and/or occupy relevant sites on the expressed marker genes which are upregulated in tissues or cells derived from MS-patients or individuals susceptible to MS.

It is furthermore envisaged that such inhibitors interfere with the synthesis/production of (functional) upregulated marker genes or gene products, like, e.g. anti-sense constructs, ribozymes and the like. The inhibitors and/or antagonist which can be screened for and obtained in accordance with the method of the present invention include, inter alia, peptides, proteins, nucleic acids including DNA, RNA, RNAi, PNA, ribozymes, antibodies, small organic compounds, small molecules, ligands, and the like.

Accordingly, the inhibitor and/or antagonist of differentially (expressed) and in MS-patients up-regulated marker genes may comprises (an) antibody(ies). Said antibody(ies) may comprise monoclonal antibodies as well as polyclonal antibodies. Furthermore, chimeric antibodies, synthetic antibodies as well as antibody fragments (like Fab, F(ab)2, Fv, scFV), or a chemically modified derivative of antibodies are envisaged. It is envisaged that said antibodies bind to said marker gene or its gene product and/or interfere its activity.

In addition, oligonucleotides and/or aptamers which specifically bind to said upregulated marker genes as defined herein or which interfere with the activity of said marker genes are envisaged as inhibitors and/or antagonists. The term "oligonucleotide" as used in accordance with the present invention comprises coding and non-coding sequences, it comprises DNA and RNA and/or comprises also any feasible derivative. The term "oligonucleotide" further comprises peptide nucleic acids (PNAs) containing DNA analogs with amide backbone linkages (Nielson, Science 274 (1991), 1497–1500). Oligonucleotides which may inhibit and/or antagonize the marker gene activity and which can be identified and/or obtained by the method of the present invention can be, inter alia, easily chemically synthesized using synthesizers which are well known in the art and are commercially available like, e.g., the ABl 394 DNA-RNA Synthesizers.

In accordance with the present invention, the term aptamer means nucleic acid molecules that can bind to target molecules, preferably to H-FABP as defined herein. Aptamers commonly comprise RNA, single stranded DNA, modified RNA or modified DNA molecules. The preparation of aptamers is well known in the art and may involve, inter alia, the use of combinatorial RNA libraries to identify binding sites (Gold, Ann. Rev. Biochem. 64 (1995), 763–797).

As mentioned herein above, said inhibitor and/or antagonist may also comprise small molecules. Said small molecules, however may also be identified as activators or agonists by the herein disclosed methods. The term "small molecule" relates, but is not limited to small peptides, anorganic and/or organic substances or peptide-like molecules, like peptide-analogs comprising D-amino acids.

Furthermore, peptidomimetics and/or computer aided design of appropriate antagonist, inhibitors, agonists or activators may be employed in order to obtain candidate compounds to be tested in the inventive method. Appropriate computer systems for the computer aided design of, e.g., proteins and peptides are described in the prior art, for example, in Berry, Biochem. Soc. Trans. 22 (1994), 1033–1036; Wodak, Ann. N. Y. Acad. Sci. 501 (1987), 1–13; Pabo, Biochemistry 25 (1986), 5987–5991. The results obtained from the above-described computer analysis can be used in combination with the method of the invention for, e.g., optimizing known compounds, substances or molecules. Appropriate compounds can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220–234 and Dorner, Bioorg. Med. Chem. 4 (1996), 709–715. Furthermore, the three-dimensional and/or crystallographic structure of inhibitors activators, agonsits or activators of the markers of the present invention or of the nucleic acid molecule encoding said expressed markers can be used for the design of peptidomimetic inhibitors, antagonsits, agonists or activators to be tested in the method of the invention (Rose, Biochemistry 35 (1996), 12933–12944; Rutenber, Bioorg. Med. Chem. 4 (1996), 1545–1558).

The compounds to be screened with the method(s) of the present invention do not only comprise single, isolated compounds. It is also envisaged that mixtures of compounds are screened with the method of the present invention. It is also possible to employ extraxts, like, inter alia, cellular extracts from prokaryotic or eukaryotic cells or organisms.

In addition, the compound identified or refined by the inventive method can be employed as a lead compound to achieve, modified site of action, spectrum of activity, organ specificity, and/or improved potency, and/or decreased toxicity (improved therapeutic index), and/or decreased side effects, and/or modified onset of therapeutic action, duration of effect, and/or modified pharmakinetic parameters (resorption, distribution, metabolism and excretion), and/or modified physico-chemical parameters (solubility, hygroscopicity, color, taste, odor, stability, state), and/or improved general specificity, organ/tissue specificity, and/or optimized application form and route may be modified by esterification of carboxyl groups, or esterification of hydroxyl groups with carbon acids, or esterification of hydroxyl groups to, e.g. phosphates, pyrophosphates or sulfates or hemi succinates, or formation of pharmaceutically acceptable salts, or formation of pharmaceutically acceptable complexes, or synthesis of pharmacologically active polymers, or introduction of hydrophylic moieties, or introduction/exchange of substituents on aromates or side chains, change of substituent pattern, or modification by introduction of isosteric or bioisosteric moieties, or synthesis of homologous compounds, or introduction of branched side chains, or conversion of alkyl substituents to cyclic analogues, or derivatisation of hydroxyl group to ketales, acetales, or N-acetylation to amides, phenylcarbamates, or synthesis of Mannich bases, imines, or transformation of ketones or aldehydes to Schiff's bases, oximes, acetales, ketales, enolesters, oxazolidines, thiozolidines or combinations thereof.

In a further embodiment, the present invention provides for a method for the preparation of a pharmaceutical composition comprising the steps of the methods disclosed herein above and a further step of formulating the compound or the plurality of compounds identified or obtained in a pharmaceutically acceptable carrier or diluent.

Accordingly the present invention also relates to a pharmaceutical composition comprising a compound or a plurality of compounds which is obtainable by the methods of the invention and a pharmaceutically acceptable carrier. Said pharmaceutical composition is in particular useful in the treatment of MS.

In a further embodiment, the invention provides for the use of a compound or a plurality of compounds which is obtainable by the method described herein for the preparation of a pharmaceutical composition for treating or preventing multiple sclerosis.

Additionally, the invention provides for the use of a compound or a plurality of compounds which is obtainable by the method disclosed herein for the preparation of a diagnostic composition for diagnosing multiple sclerosis or a predisposition for multiple sclerosis. It is, for example envisaged that specific antibodies) fragments thereof or derivatives thereof which specifically detect or recognize differentially expressed marker gene products as disclosed herein be employed in such diagnostic compositions. Yet, specific primers/primer pairs which may detect and/or amplify the marker gene of the present invention may be employed in said diagnostic compositions.

Accordingly, the compound to be used in the pharmaceutical as well as in the diagnostic composition may comprises an antibody, an antibody-derivative, an antibody fragment, a peptide or a nucleic acid, like primers/primer pairs as well as anti-sense constructs, RNAi or ribozymes.

The diagnostic composition may also comprise suitable means for detection known in the art.

The invention is further described by reference to the following biological examples which are merely illustrative and are not to be construed as a limitation of scope.

EXAMPLES

Example 1

Preparation of RNA-samples Derived Form MS Patients and Healthy Volunteers

Eight patients (5 women, 3 men) with clinically definite or laboratory-supported definite multiple sclerosis (Poser et al., 1983) were included (Table 1: EDSS (expanded disability status scale, after Kurtzke, Neurology 33, 1444–52, 1983) represents a scale for objecti-vating the disability caused by MS (range 0 (no symptoms) to 10 (death by MS)); MRI (magnetic resonance imaging)). All patients had relapsing-remitting (RRMS) disease in remission without any treatment. None of the patients had received corticosteroids or other immunosuppressive agents within 6 weeks prior to the sampling. Eight age and gender-matched healthy volunteers were used as controls.

Human peripheral blood mononuclear cells (PBMCs) were separated from 30 ml blood by density gradient centrifugation employing Ficoll-Hypaque (Sigma Chemical, St Louis, Mo.). The cells were counted and suspended in 1 ml RNAzol. For RNA isolation the cells were disrupted in FastPrep tubes in RNAzol for 20 seconds in a Savant homogenizer (Bio101, Buena Vista, Calif., U.S.A.). Total RNA was isolated according to the manufacturer's instruction and DNAse I treatment (Ambion, Austin, Tex., U.S.A.) was applied to eliminate genomic DNA interference. The quality of RNA was assessed with gel electrophoresis.

Example 2

Synthesis and Hybridization of cRNA

Double strand cDNA was synthesized from 20 µg of total RNA using cDNA Synthesis System (Roche Diagnostics, Mannheim, Germany) with the oligo(dT)$_{24}$ T7prom)$_{65}$ primer. The MEGAScript T7 kit (Ambion, Austin, Tex., U.S.A.) was used to transcribe the cDNA into cRNA in the presence of Biotin-11-CTP and Biotin-16-UTP (Enzo, Farmingdale, N.Y., U.S.A.) according to the instructions supplied with the kit. After purification with the RNeasy kit (Qiagen, Hilden, Germany) integrity of the cRNA was checked using gel electrophoresis. 10–20 µg fragmented cRNA were used for hybridization to the HuGeneFL array (Affymetrix GeneChip® array, Santa Clara, Calif.). Hybridization and staining were performed as described previously (Lockhardt et al., 1996; de Saizieu et al., 1998). Arrays were scanned with a confocal laser scanner (Hewlett-Packard, Palo Alto, Calif., USA).

Example 3

Expression Analysis and Data Validation

Fluorescence intensities were analyzed with the GENE-CHIP 3.1 software (Affymetrix) and expression data were analyzed with RACE-A program (Hoffmann-La Roche, Basel, Switzerland). The expression level (average difference) for each gene was determined by calculating the average of differences in intensity (perfect match-mismatch) between its probe pairs. CLUSTER and TREEVIEW were used to select, group and visualize genes whose expression varied across the samples. Candidate marker genes were categorized in the following: a) differentially expressed genes (upregulated in MS and absent/low expression in controls, change factor>2, p<0.01, purity>0.6), b) highly expressed genes in both groups, but up- or downregulated in MS (change factor >0.5 or <−0.5, p<0.01, purity>0.6), c) cytokines and related molecules, d) MHC complex associated genes, e) matrix metalloproteinases and their regulators, and f) unchanged genes with constitutive expression in both MS and in controls.

The oligonucleotide array used in the present study contains probe sets for over 6000 human genes. After hybridization and scanning, the fluorescence intensity of each gene was calculated by subtracting the mismatch from the match signal (=average difference). Genes with average hybridization intensities<200 were considered absent in a sample. Two data sets (MS patients vs. healthy subjects) were compared. Difference of means, change factor (>2 or <−2), statistical significance (unpaired t-test, p<0.01) and purity of samples (>0.6) were applied. 51 differentially expressed genes were identified. 11 of them were absent in all control samples (n=8) and were variably expressed in MS samples (4–7 of 8 samples) (Tables 2, 3 and 4). In addition of these 11 genes, five other targets from this category were chosen as possible marker genes for MS. With less stringent filtering criteria (change factor>0.5 or <−0.5, p<0.05) 12 other genes were selected. These included cytokines, MHC complex associated genes and highly expressed genes. Also five constitutively and equally expressed targets in both sample groups were named as quality controls of the analysis.

Matrix metalloproteinase-9 (MMP-9), tumor necrosis factor-α (TNF-α) and lymphotoxin-β were upregulated in average in MS samples compared to those of control subjects (change factors 1.38, 8.68 and 0.52, respectively), but these differences did not reach statistical significance (Table 3). Several reports have shown upregulation of MMP-9, TNF-α and lymphotoxin-β in MS patients, therefore these genes were included for further analysis with real-time PCR.

The real-time PCR is truly quantitative method, while genechip-analysis is only semi-quantitative for transcriptional expression studies. Total 36 candidate genes (Tables 2, 3 and 4) as possible diagnostic and predictive molecular markers for MS were carried on for verification studies with real-time PCR.

The selected genes were validated as markers with "blind" samples. 20 randomly collected samples from healthy volunteers and RRMS patients in remission without treatment were analyzed with real-time PCR using specific hybridization probes as described above. Samples were categorized into patient and control groups based on the expression level of marker genes. The "blinded" code was opened and results evaluated. Validation of expression of candidate marker genes with real-time PCR was carried out as follows:

Specific primers for 30 have been designed in order to evaluate the expression with RT-PCR using SybrGreen assay. Six genes were analyzed with highly specific TaqMan probes with commercially available pre-developed assay reagents (PDAR) provided by Applied Biosystems (PE Europe B.V., Rotkreuz, Switzerland). The specificity of the SybrGreen assay was evaluated with dissociation curve software (Applied Biosystems).

TABLE 1

| Code | Gender | Age | Duration of disease (years) | EDSS | MRI (Gd) |
|---|---|---|---|---|---|
| MS 1 | F | 38 | 5.3 | 1.5 | +1 |
| MS 2 | M | 30 | 3 | 1.0 | +1 |
| MS 3 | F | 58 | 28 | 2.5 | −0 |
| MS 4 | F | 42 | 2.3 | 2.5 | −0 |
| MS 5 | F | 40 | 21 | 1.5 | −0 |
| MS 6 | M | 22 | 4.4 | 2 | +1 |
| MS 7 | F | 29 | 5 | 1.5 | +3 |
| MS 8 | F | 33 | 8 | 1.5 | −0 |

TABLE 2

| No | Affy-ID Genbank | Description | Change factor | Code | SybrGreen conditions Forward primer | Reverse primer | Amplicon (bp) |
|---|---|---|---|---|---|---|---|
| 1 | L11329 | homo sapiens protein tyrosine phosphatase (pac-1) mrna, complete cds | 68.45 | PAC-1 | 50 | 300 | 99 |
| 2 | D42040 | human mrna for kiaa9001 gene, complete cds | 56.8 | RING | 300 | 900 | 71 |
|  | X62083 | h. sapiens mrna for drosophila female sterile homeotic (fsh) homologue | 5.86 |  |  |  |  |
| 3 | Z30426 | h. sapiens gene for early lymphocyte activation antigen cd69, exon 1 | 26.7 | CD69 | — | — | — |
| 4 | L20859 | human leukemia virus receptor 1 (glvr1) mrna, complete cds | 9.2 | GLVR1 | 50 | 300 | 69 |
| 5 | M31899 | human dna repair helicase (ercc3) mrna, complete cds | 8.94 | ERCC3 | 300 | 300 | 143 |
| 6 | U02020 | human pre-b cell enhancing factor (pbef) mrna, complete cds | 4.11 | PBEF | 900 | 900 | 99 |
| 7 | M59465 | human tumor necrosis factor alpha inducible protein a20 mrna, complete cds | 3.75 | A20 |  |  | 60 |
| 8 | D13627 | human mrna for kiaa0002 gene, complete cds | 3.7 | KIAA2 | 900 | 300 | 77 |
| 9 | Z11697 | homo sapiens mrna for hb15, CD83 | 3.36 | HB15 | 300 | 300 | 107 |
| 10 | U19523 | human gtp cyclohydrolase i mrna, complete cds | 4.78 | GTPHY1 | 300 | 900 | 100 |
| 11 | U25849 | human red cell-type low molecular weight acid phosphatase (acp1) gene, 5prime flanking region and | 26.05 | ACP1 | 300 | 300 | 104 |
| 12 | U50078 | human guanine nucleotide exchange factor p532 mrna, complete cds | 2.71 | GEF |  |  | 136 |
| 13 | X59405 | h. sapiens, gene for membrane cofactor protein, CD46 | 2.49 | MCP | 900 | 900 | 76 |
| 14 | Z56281 | h. sapiens mrna for interferon regulatory factor 3 | 2.28 | IRF3 | 900 | 900 | 73 |
| 15 | L10717 | homo sapiens t cell-specific-tyrosine kinase mrna, complete cds | 3.05 | TcsTK | 300 | 50 | 80 |
| 16 | M31951 | human perforin (prf1) gene, complete cds | −24.29 | Perf | 300 | 300 | 71 |
| 17 | M32315 | human tumor necrosis factor receptor mrna, complete cds | 0.64 | TNFR2 | 900 | 900 | 148 |
| 18 | U15085 | human hla-dmb mrna, complete cds | 0.61 | HLADMB | 300 | 300 | 98 |
| 19 | Y00062 | human mrna for t200 leukocyte common antigen (cd45, lc-a) | 0.7 | CD45 | 900 | 300 | 73 |
| 20 | M92843 | h. sapiens zinc finger transcriptional regulator mrna, complete cds | 0.85 | TTP | 300 | 300 | 70 |
| 21 | M85276 X54101 | homo sapiens nkg5 gene, complete cds mRNA | −0.9 | NKG5 | 900 | 300 | 61 |
| 22 | X14046 | human mrna for leukocyte antigen cd37 | −0.71 | CD37 | 900 | 50 | 122 |
| 26 | U19247 | human interferon-gamma receptor alpha chain gene | 1.58 | IFNγRα | 300 | 900 | 126 |
| 27 | U05875 | human clone psk1 interferon gamma receptor accessory factor-1 (af-1) mrna, complete cds | 1.16 | AF1 | 300 | 300 | 121 |
| 28 | X04500 X56087 | human gene for prointerleukin 1 beta mRNA | 4.85 | ProIL1β | 900 | 900 | 112 |

TABLE 2-continued

| Affy-ID No Genbank | Description | Change factor | Code | SybrGreen conditions | | |
|---|---|---|---|---|---|---|
| | | | | Forward primer | Reverse primer | Amplicon (bp) |
| 29 U00672 | human interleukin-10 receptor mrna, complete cds | 1.59 | IL10R | 50 | 900 | 73 |
| 30 M16276 | human mhc class ii hla-dr2-dw12 mrna dqw1-beta, complete cds | 21.15 | HLADRB | 900 | 300 | 110 |
| 31 X65463 | h. sapiens mrna for mhc class i promoter binding protein | 22.4 | MHCI-PBP | 300 | 300 | 84 |

TABLE 3

| Affy-ID No Genbank | Description | Change factor | Code | SybrGreen conditions | | |
|---|---|---|---|---|---|---|
| | | | | Forward primer | Reverse primer | Amplicon (bp) |
| 23 J05070 | human type iv collagenase mrna, complete cds | 1.38 | MMP9 | — | — | — |
| 24 X02910 | human gene for tumor necrosis factor (tnf-alpha) | 8.68 | TNFα | — | — | — |
| 25 U89922 | human lymphotoxin beta isoform variant, alternatively spliced mrna, complete cds | 0.52 | Lympho-β | — | — | — |

TABLE 4

| Affy-ID No Genbank | Description | Change factor | Code | SybrGreen conditions | | |
|---|---|---|---|---|---|---|
| | | | | Forward primer | Reverse primer | Amplicon (bp) |
| 32 M33197 | GAPDH (Chip and PDAR) | −0.41 | GAPDH | — | — | — |
| 33 ? | Ribosomal RNA control (18S rRNA) | −0.41 | 18SrRNA | — | — | — |
| 34 M86400 | human phospholipase a2 mrna, complete cds | 0 | PLA2 | 900 | 900 | 139 |
| 35 D00017 | human lipocortin ii mrna | −0.01 | LCII | 300 | 900 | 62 |
| 36 M75126 | human hexokinase 1 (hk1) mrna, complete cds | 0 | HK1 | 900 | 300 | 81 |

What is claimed is:

1. An in vitro method for the diagnosis of multiple sclerosis or the susceptibility to multiple sclerosis comprising the steps of:
   (a) providing a biological sample;
   (b) measuring the expression level of the human protein tyrosine phosphatase gene (PAC-1) in the biological sample; and
   (c) providing either 1) a diagnosis of multiple sclerosis or an increased susceptibility to multiple sclerosis if the expression level is increased or 2) a diagnosis of decreased susceptibility to multiple sclerosis if the expression level is not increased.

2. The in vitro method of claim 1, wherein said biological sample is derived from the group consisting of blood, nervous tissue, cerebrospinal fluid or brain tissue.

3. The in vitro method of claim 1, wherein measuring step (b) is carried out by measuring the amount of nucleic acid molecules coding for polypeptides encoded by the human protein tyrosine phosphatase gene.

4. The in vitro method of claim 3, wherein said nucleic acid molecule is RNA or DNA.

5. The in vitro method of claim 4, wherein said DNA is a cDNA.

6. The in vitro method of claim 1, wherein said measuring step (b) is carried out by measuring the amount of a polypeptide or a fragment thereof encoded by the human protein tyrosine phosphatase gene.

7. The in vitro method of claim 1, wherein the expression level of the human protein tyrosine phosphatase gene in a biological sample is compared to the expression level of the human protein tyrosine phosphatase gene in a healthy individual.

8. The in vitro method of claim 7, wherein an increase of the expression level in the human protein tyrosine phosphatase gene is an indicator of multiple sclerosis or the susceptibility to multiple sclerosis.

9. The in vitro method of claim 1, further comprising measuring the expression level of one or more genes other than human protein tyrosine phosphatase.

10. The in vitro method of claim 9, wherein expression levels of the genes are measured using an oligonucleotide array.

11. The in vitro method of claim 9, wherein expression levels of the genes are measured using real time PCR.

* * * * *